US009926592B2

(12) United States Patent
Armitage et al.

(10) Patent No.: US 9,926,592 B2
(45) Date of Patent: Mar. 27, 2018

(54) GAMMA-PNA MINIPROBES FOR FLUORESCENT LABELING

(71) Applicants: CARNEGIE MELLON UNIVERSITY, Pittsburgh, PA (US); UNIVERSITY OF PITTSBURGH—OF THE COMMONWEALTH SYSTEM OF HIGHER EDUCATION, Pittsburgh, PA (US)

(72) Inventors: Bruce A. Armitage, Pittsburgh, PA (US); Patricia L. Opresko, Pittsburgh, PA (US); Danith Ly, Pittsburgh, PA (US); Nathaniel Shank, Pittsburgh, PA (US)

(73) Assignees: CARNEGIE MELLON UNIVERSITY, Pittsburgh, PA (US); UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 189 days.

(21) Appl. No.: 14/357,874

(22) PCT Filed: Nov. 14, 2012

(86) PCT No.: PCT/US2012/064976
§ 371 (c)(1),
(2) Date: May 13, 2014

(87) PCT Pub. No.: WO2013/074601
PCT Pub. Date: May 23, 2013

(65) Prior Publication Data
US 2015/0197793 A1   Jul. 16, 2015

Related U.S. Application Data

(60) Provisional application No. 61/629,125, filed on Nov. 14, 2011.

(51) Int. Cl.
*C12Q 1/68* (2018.01)
*G01N 33/533* (2006.01)
*C12N 15/113* (2010.01)

(52) U.S. Cl.
CPC .......... *C12Q 1/6825* (2013.01); *C12N 15/113* (2013.01); *C12Q 1/6816* (2013.01); *G01N 33/533* (2013.01); *C12N 2310/3181* (2013.01); *C12N 2320/10* (2013.01)

(58) Field of Classification Search
None
See application file for complete search history.

(56) References Cited

U.S. PATENT DOCUMENTS

| | | | | |
|---|---|---|---|---|
| 5,854,033 A | * | 12/1998 | Lizardi | C12Q 1/6804 435/6.12 |
| 6,329,144 B1 | * | 12/2001 | Kubista | C07D 417/06 435/6.1 |
| 6,514,693 B1 | | 2/2003 | Lansdorp | |
| 2003/0022204 A1 | * | 1/2003 | Lansdorp | C12Q 1/6841 435/6.18 |
| 2003/0082543 A1 | * | 5/2003 | Su | C12Q 1/6855 435/6.12 |
| 2008/0261822 A1 | | 10/2008 | Fejgin et al. | |
| 2008/0280776 A1 | * | 11/2008 | Bashir | G01N 27/127 506/9 |

FOREIGN PATENT DOCUMENTS

| | | |
|---|---|---|
| KR | 10-2011-0098405 | 9/2011 |
| WO | WO-2008/081451 | 7/2008 |
| WO | WO-2011/028494 A2 | 3/2011 |
| WO | WO-2012/138955 A2 | 10/2012 |

OTHER PUBLICATIONS

Englund (Org Lett 2005 vol. 7 p. 3467).*
Hultdin et al. (Nucleic Acids Research 1998 vol. 26 p. 3651-3656).*
He et al. (Mol Biosyst Sep. 2010 vol. 6 p. 1619-1629).*
Chenna et al. (ChemBioChem 2008 vol. 9 p. 2388-2391).*
Lusvarghi et al. (J. Am. Chem 2009 vol. 131 p. 18415).*
Sforza et al. (Eur J Org Chem 1999 p. 197).*
Englund et al., "Synthesis of Gamma-Substituted Peptide Nucleic Acids: A New Place to Attach Fluorophores Without Affecting DNA Binding," Organic Letters, vol. 7, No. 16, pp. 3465-3467, May 16, 2005.
International Search Report and the Written Opinion of the International Searching Authority dated Mar. 26, 2013 issued in connection with International Application No. PCT/US2012/064976.
Baerlocher, et al., "Telomere Length Measurement by Fluorescence In Situ Hybridization and Flow Cytometry: Tips and Pitfalls", Cytometry, 47:89-99, 2002.
Blackburn et al. "The Molecular Structure of Centromeres and Telomeres", Am. Rev. Biochem, 53:163-194, 1984.
Cech, "Life at the End of the Chromosomes: Telomeres and Telomerase", Angew. Chem. Int. Ed., 39:34-43, 2000.
Christensen et al., "Solid-phase Synthesis of Peptide Nucleic Acids", Journal of Peptide Science, vol. 3, pp. 175-183, 1995.
Dragulescu-Andrasi et al., "A Simple γ-Backbone Modification Preorganizes Peptide Nucleic Acid into a Helical Structure," JACS Articles, 128, 10258-10267, Aug. 2006.
Egholm et al., "PNA hybridizes to complementary oligonucleotides obeying the Watson-Crick hydrogen-bonding rules", Nature, vol. 35, Oct. 1993.
European Search Report dated May 13, 2015 issued in European Application No. EP12849889.
Gavory et al., "Structural Analysis of the Catalytic Core of Human Telomerase RNA by FRET and Molecular Modeling," Biochemistry, 45, 13304-13311, Nov. 2006.

(Continued)

*Primary Examiner* — Katherine D Salmon
(74) *Attorney, Agent, or Firm* — Foley & Lardner LLP

(57) ABSTRACT

A category of γPNA miniprobes and chimeric γPNA probes is especially useful for detecting RNA and telomeric DNA in a cell sample. In particular, the probes can be used to deliver fluorescent dyes to the telomeres, allowing direct visualization of telomeres in cells.

23 Claims, 9 Drawing Sheets

(56) References Cited

OTHER PUBLICATIONS

Lansdorp et al., "Heterogeneity in telomere length of human chromosomes", Human Molecular Genetics, vol. 5, No. 5, pp. 685-691, 1996.
Lansdorp, "Telomeres and disease", The EMBO Journal, vol. 28, No. 17, pp. 2532-2540, Jul. 2009.
Rapireddy et al., "Strand Invasion of Mixed Sequence B-DNA by Acridine-Linked, y-Peptide Nucleic Acid (y-PNA)," J. Am. Chem. Soc., 129, 15596-15600, Dec. 2007.
Sahu et al., "Synthesis and Characterization of Conformationally Preorganized, (R)-Diethylane Glycol-Containing y-Peptide Nucleic Acids with Superior Hybridization Properties and Water Solubility," The Journal of Organic Chemistry, 76, 5614-5627, Jul. 2011.
Yeh et al., "Crystal Structure of Chiral yPNA with Complementary DNA Strand: Insights into the Stability and Specificity of Recognition and Conformational Preorganization", J. Am. Chem. Soc., 132:10717-10727, 2010.

\* cited by examiner

| Probe | Sequence |
|---|---|
| PNA | Cy3-(CCCTAA)$_3$-LysNH$_2$ |
| γPNA-1 | Cy3-(<u>CCCTAA</u>)$_2$-LysNH$_2$ |
| γPNA-2 | Cy3-<u>CCCTAA</u>-LysNH$_2$ |
| γPNA-3 | Cy3-<u>XCXTAA</u>-LysNH$_2$ |
| Telo-X | 5'-(TTAGGG)$_x$-3' |

SEQUENCE LISTING

```
<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      peptide nucleic acid sequence
<220> FEATURE:
<221> NAME/KEY: misc_feature
<222> LOCATION: (1)..(10)
<223> OTHER INFORMATION: PNA sequence

<400> SEQUENCE: 1
cgattttcga                                                          10

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      peptide nucleic acid sequence
<220> FEATURE:
<221> NAME/KEY: misc_feature
<222> LOCATION: (1)..(18)
<223> OTHER INFORMATION: PNA sequence

<400> SEQUENCE: 2
aatcccaatc ccaatccc                                                 18

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      peptide nucleic acid sequence
```

```
-continued

<220> FEATURE:
<221> NAME/KEY: misc_feature
<222> LOCATION: (1)..(12)
<223> OTHER INFORMATION: PNA sequence

<400> SEQUENCE: 3
aatcccaatc cc                                                          12
```

GAMMA-PNA MINIPROBES FOR FLUORESCENT LABELING

CROSS-REFERENCE TO RELATED PATENT APPLICATIONS

This application claims priority to U.S. provisional application No. 61/629,125, filed Nov. 14, 2011, the entire contents of which are incorporated herein by reference.

GOVERNMENT RIGHTS

This invention was made with United States government support under Grant No. ES0515052 awarded by the National Institutes of Health. The United States government has certain rights in this invention.

SEQUENCE LISTING

The instant application contains a Sequence Listing which has been submitted electronically in ASCII format and is hereby incorporated by reference in its entirety. Said ASCII copy, created on Oct. 10, 2014, is named 101700-0110_SL.txt and is 1,339 bytes in size.

BACKGROUND OF THE INVENTION

Telomeric DNA is found at the extreme ends of chromosomes in humans and most other organisms. See Blackburn, E. H. and J. W. Szostak, *Annu. Rev. Biochem* 1984, 53, 164-94 and Cech, T. R. *Angew. Chem. Int. Ed.* 2000, 39, 35-43. Telomeres are characterized by a repeat sequence motif which in humans is 5'-TTAGGG-3. This sequence is repeated tens or even hundreds of times through each end of the double-stranded region of the chromosome and beyond, into a single-stranded extension on the 3'-terminus at each end. The telomeres naturally become shorter with each round of cell division until a critical threshold is reached, after which cellular growth arrest (senescence) occurs. Critically short telomeres have been implicated in a range of aging-related diseases. In addition, maintenance of stable telomere lengths, either through the action of the telomerase enzyme or through alternative mechanisms, is a hallmark of cancer cells. See Lansdorp, P. M., *EMBO J.* 2009, 28, 2532-40

Given the great interest in telomere biology, methods that permit analysis of the integrity and length of telomeres are widely used in research and diagnostic medicine. One such method involves the in situ hybridization of a fluorescent PNA probe to the telomere. See Baerlocher, G. M., et al., *Cytometry* 2002, 47, 89-99, and Lansdorp, P. M., et al., *Hum. Mol. Gen.* 1996, 5, 685-91. The conventional PNA probe is 18 nucleobases (18-mer) in length and is complementary to three contiguous repeats of the human telomere sequence. A fluorescent dye such as Cy3 is attached to the PNA N-terminus, which permits imaging of the telomeres via fluorescence microscopy and quantitative analysis by flow cytometry.

Fewer fluorescently labeled PNA probes are able to hybridize to the telomere, however, as telomeres become shorter or are damaged. As a result, the fluorescent signal observed becomes weaker which hampers intracellular visualization of telomeres and their quantitative analysis under biological conditions that promote telomere shortening.

The conventional choice for using a fluorescently labeled PNA rather than a DNA oligonucleotide probably stems from the observation that PNA's exhibit higher hybridization affinity for complementary DNA targets compared with other synthetic DNA analogues. See Egholm, M et al., *Nature* 1993, 365, 566-68. It was observed, moreover, that an even higher binding affinity can be obtained by introducing one or more substituent groups into the PNA backbone, particularly when the substituent group is introduced at the gamma carbon (γ-C) atom of the PNA monomer. See Dragulescu-Andrasi, A., et al., *J. Am. Chem. Soc.* 2006, 128, 10258-67. These "γPNAs" (gamma-PNAs), developed by Ly and coworkers, exhibit a helical pre-organization and improved water solubility compared with standard PNA. See FIG. 1 below and Yeh, J. I., et al., *J. Am. Chem. Soc.* 2010, 132, 10717-27, and Sahu, B., et. al., *J. Org. Chem.* 2011, 76, 5614-27.

SUMMARY OF THE INVENTION

To avoid the disadvantages of conventional PNA probes, therefore, the present invention provides, in one of its aspects, a γPNA probe, comprising (A) a single-domain PNA oligomer or (B) a two-domain PNA oligomer comprising (i) a first domain and a second domain, where the first domain is shorter than the second domain, and (ii) a detectable label that is covalently attached to the first domain or the second domain. In the instance of a single-domain PNA oligomer, the oligomer can be a γPNA miniprobe that comprises six PNA monomers, nine PNA monomers, or 12 PNA monomers.

In one embodiment of the two-domain PNA oligomer, the first and second domains of the γPNA probe are covalently attached end-to-end to form a chimeric γPNA probe, where (A) the first domain comprises from 6 to 10 right-handed PNA monomers; (B) the second domain comprises from 4 to 6 left handed PNA monomers; and (C) at least one of the PNA monomers in the first domain, in the second domain, or in both the first and second domains is a γPNA monomer. In such a chimeric γPNA probe, the sequence of the first domain can be complementary to a telomeric DNA, in which case the second domain does not hybridize with the telomeric DNA. In one embodiment the first domain of a chimeric γPNA probe comprises nine right-handed PNA monomers and the second domain comprises six left-handed monomers.

In another aspect, the invention provides a kit for detecting a telomeric DNA in a cell sample via use of the single-domain or two-domain γPNA probes mentioned above. Thus, an inventive kit can comprise at least two receptacles, where (A) one of receptacles contains a γPNA miniprobe that hybridizes with the telomeric DNA and (B) another of the receptacles contains a diluent suitable for hybridization. The γPNA miniprobe employed in this context can comprise, as a detectable label, at least one fluorescent dye selected from the group consisting of Cy3, Cy3B, Cy3.5, Cy5, Cy5.5, Cy7, coumarin, acridine derivatives, eosin derivatives and fluorescein. In such a γPNA miniprobe the detectable label can be attached to a N-terminal or a C-terminal PNA monomer, to a N-terminal or a C-terminal γPNA monomer, an internal PNA monomer, or an internal γPNA monomer of the γ PNA miniprobe. Also, the detectable label can be attached to the γPNA monomer using a linker, for example, a —CH$_2$—(O—CH$_2$—CH$_2$)$_n$—X linker where X is selected from the group consisting of —NH$_2$—, —CH=CH—, —COOH and —N$_3$ and n is an integer from 1 to 10.

The invention further provides methodology for detecting telomeric DNA in a cell sample by (a) contacting the sample with one or more γPNA miniprobes as described above, each miniprobe comprising a detectable label and at least one γPNA monomer; and (b) then incubating the sample to permit the one or more γPNA miniprobes to bind adjacent positions along the length of the telomeric DNA in the sample. The first γPNA miniprobe comprising a first detectable label and the second γPNA miniprobe comprising a second detectable label form a donor-acceptor pair, such that the emission spectrum of the first detectable label overlaps with the absorption spectrum of the second detectable label. The first and second γPNA miniprobes, moreover, have different sequences to permit the first and second γPNA miniprobes to bind adjacent positions along the telomeric DNA.

In a further aspect the invention provide a method, using a chimeric γPNA probe as described, for detecting telomeric DNA in a cell sample. Accordingly, an equimolar mixture of a first chimeric γPNA probe comprising a first detectable label and a second chimeric γPNA probe comprising a second detectable label is contacted with a sample. The sample is incubated with the first and the second chimeric γPNA probes to form a donor-acceptor pair and the telomeric DNA in the sample binds the donor-acceptor pair. The chimeric γPNA probe comprises two domains, a first domain consisting from 6 to 10 right-handed PNA monomers and a second domain consisting from 4 to 6 left handed PNA monomers. The second domain of the first and second chimeric γPNA probes have complementary sequences.

According to this methodology, the first detectable label is covalently attached to the second domain of the first chimeric γPNA probe and the second detectable label is covalently attached to the first domain of the second chimeric γPNA probe. This permits the first and second detectable labels that are fluorescent dyes to form a donor-acceptor pair.

DETAILED DESCRIPTION OF THE PREFERRED EMBODIMENTS

Figures 1, 2:
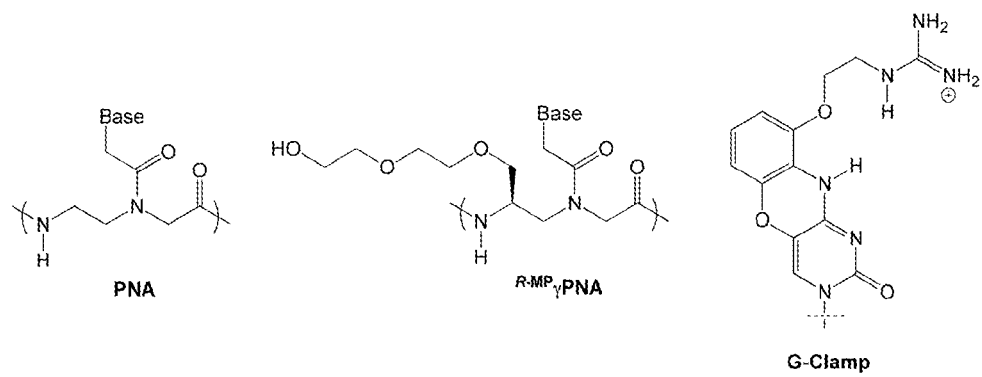
FIG. 1 shows the chemical structures of a PNA, a mini-PEG-modified γPNA, and a G-Clamp nucleobase.
FIG. 2 presents the sequences of PNA and γPNA probes (SEQ ID NOS 2-3, respectively, in order of appearance) and DNA targets. Underlined residues have gamma miniPEG substituents, while "X" corresponds to G-clamp nucleobases.

Fluorescently labeled PNA probes have been used for detecting cellular DNA or RNA including, for the detection and imaging of telomeric DNA, which is found at the extreme ends of chromosomes in most organisms. Here the phrase "telomeric DNA" denotes a DNA-oligonucleotide that is characterized by the presence of a 5'-TTAGGG-3' sequence repeated from thirteen times to several thousand times. See Capper, R. et al *Genes Devel.* 2007, 21, 2495-2508 and Calado, R.; Young, N. *F1000 Med. Rep.* 2012, 4:8.

Conventional fluorescent PNA probes used for detecting telomeric DNA in cell samples are 18 nucleobases in length. This length is necessary to permit the fluorescent PNA probe to effectively hybridize by non-covalent, sequence specific interactions over three contiguous repeat units of a human telomeric DNA. The terms "hybridization" or "hybridizing" refer to the process of establishing a non-covalent, sequence-specific interaction between two or more complementary strands of a DNA, between complementary strands consisting of a DNA and a RNA, a DNA and a PNA, a RNA and a PNA, or non-covalent, sequence-specific interactions between two PNA strands.

A disadvantage of the conventional 18-mer PNA probe, however, is its inability to effectively hybridize to short telomere sequences often present in diseased or aging cells. This results in a decrease in the intensity of the fluorescent signal and limits the utility of fluorescently labeled 18-mers as probes for the detection and visualization of a telomeric DNA or RNA in a cell sample.

Backbone-modified peptide nucleic acids (PNAs) featuring substituent groups at the γ carbon, however, exhibit a greater affinity for hybridizing to a complementary DNA strand relative to unmodified PNA. Exemplary of one such γ carbon modified PNA monomer is the mini-PEG modified γ-PNA ($^{RMP}$γ-PNA) structurally illustrated in FIG. 1.

To leverage the greater hybridization affinity of γ-PNAs the present invention provides a category of shorter γ-PNA probes that are especially effective at detecting telomeric DNA. The category of "γ-PNA probe" includes PNA oligomers having at least one γ-PNA monomer and at least one detectable label. The γ-PNA probe can have one domain or two domains, where a "domain" refers to a PNA oligomer that has a specific sequence and at least one γPNA monomer. When two domains are present in a γ-PNA probe, both domains can have the same sequence or each domain can have a different sequence. A detectable label can be covalently attached to an end PNA monomer or an internal PNA monomer of a single domain or multiple detectable labels, such as fluorescent dyes can be attached within a single domain. For a two domain γ-PNA probe, the detectable label can be attached to an end or internal PNA monomer in the first domain or the second domain. As further described below, it was surprising to observe that the γ-PNA probes of the invention can hybridize to telomeres with complex secondary structures.

The γ-PNA probe category of the invention includes (1) γ-PNA miniprobes and (2) chimeric γ-PNA probes. A γ-PNA miniprobe is a PNA oligomer having a single domain and at least one detectable label. The domain can have six PNA monomers, nine PNA monomers, or twelve PNA monomers and at least one of the monomers is a γ-PNA moiety. The sequences of the inventive γ-PNA miniprobes are designed to be complementary to the sequence 5'-TTAGGG-3' that repeats in a telomere. γ-PNA miniprobes having six, nine and twelve monomers, therefore, bind to one, one and a half (1.5) and two contiguous repeats, respectively, of a telomere. A "chimeric γ-PNA probe," is a PNA oligomer that has two domains which are connected end-to-end and a detectable label. The first and second domains of the inventive chimeric γ-PNA probe contain PNA monomers of opposing chirality and each domain has at least γ-PNA monomer. Accordingly, the inventive chimeric γ-PNA probe has a first domain having right-handed PNA monomers while the second domain has left-handed PNA monomers. The sequence of the first domain is complementary to the sequence of a target telomere, while the sequence of the second domain is not complementary to the sequence of the telomere.

For detecting telomeric DNA with the chimeric γ-PNA probes an equimolar mixture is used in which approximately one half of the probes have a fluorescent label in the first domain. The remaining probes have a fluorescent label in the second domain. Thus, the phrase "equimolar mixture" denotes a mixture having equal moles of the two chimeric γ-PNA probes.

The invention contemplates methods for using the γ-PNA miniprobes or the chimeric γ-PNA probes to detect telomeric DNA in a cell sample or from a cell sample. The inventive γ-PNA miniprobes or chimeric γ-PNA probes can be packaged in a kit for detecting telomeric DNA. Such a kit would contain a known amount of the inventive γ-PNA miniprobes or an equimolar mixture of the chimeric γ-PNA probes and a diluent as further described below.

Accordingly, the inventive kit will comprise at least two receptacles. One receptacle will contain a γPNA miniprobe or the chimeric γ-PNA probes while the other receptacle will contain an appropriate diluent, for instance a diluent that promotes denaturation of the telomeric DNA and hybridization of the inventive γPNA miniprobe or chimeric γ-PNA probes to telomeric DNA.

The γPNA miniprobe may be provided as a lyophilized powder or as a buffered solution. The amount of γPNA miniprobe present in the receptacle can vary from an amount sufficient for single use to amounts necessary for multiple uses. Thus, the amount of the γPNA miniprobe will be from about 0.01 µg to about 100 µg, such as about 0.1 µg, 1 µg, 5 µg, 10 µg, 20 µg, 30 µg, 40 µg, 50 µg, 60 µg, 70 µg, 80 µg, 90 µg, or 100 µg.

The diluent supplied in the kit can be water, buffer, a mixture of buffer and one or more reducing agents and a denaturant such as a solution of sodium chloride. Suitable buffers include TRIS, HEPES, PIPES, phosphate buffer and acetate buffer. The buffers may contain one or more reducing agents. Exemplary reducing agents include without limitation tris(2-carhoxyethyl)phosphine (TCEP), β-mercaptoethanol, thionein, dithiothreitol (DTT). The kit may optionally contain a washing solution for removing unhybridized probe or remnants of free dye that can contribute to the background signal.

Dyes typically conjugated to the γPNA miniprobes or chimeric γPNA probes described above are Cy3, Cy5, Cy7, Cy3B, Cy3.5, Cy5.5, coumarin, acridine derivatives, eosin derivatives and fluorescein. Other detectable groups, such as gold or silver nanoparticles that can be detected by electron microscopy can also be used as detectable labels. The dye can be attached to a N-terminal or a C-terminal PNA monomer, to a N-terminal or a C-terminal γPNA monomer, an internal PNA monomer, or an internal γPNA monomer of the γ PNA miniprobe. The detectable label can be attached to the γPNA monomer using a linker, for example, a —$CH_2$—(O—$CH_2$—$CH_2$)$_n$—X linker where X is selected from the group consisting of —$NH_2$—, —CH≡CH—, —COOH, C(O)R and —$N_3$ and n is an integer from 1 to 10. When X is —C(O)R, substituent R is selected from —O($C_1$-$C_{10}$) alkyl, —O($C_3$-$C_{14}$) aryl, or a halogen, such as chlorine, bromine, iodine or fluorine.

The term "alkyl" denotes straight, branched chain, or cyclic hydrocarbyl groups including from 1 to about 20 carbon atoms. For instance, an alkyl can have from 1 to 10 carbon atoms or 1 to 5 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH($CH_3$)$_2$, —CH($CH_3$)($CH_2CH_3$), —CH($CH_2CH_3$)$_2$, —C($CH_3$)$_3$, —C($CH_2CH_3$)$_3$, —$CH_2$CH($CH_3$)$_2$, —$CH_2$CH($CH_3$)($CH_2CH_3$), —$CH_2$CH($CH_2CH_3$)$_2$, —$CH_2$C($CH_3$)$_3$, —$CH_2$C($CH_2CH_3$)$_3$, —CH($CH_3$)CH($CH_3$)($CH_2CH_3$), —$CH_2CH_2$CH($CH_3$)$_2$, —$CH_2CH_2$CH($CH_3$)($CH_2CH_3$), —$CH_2CH_2$CH($CH_2CH_3$)$_2$, —$CH_2CH_2$C($CH_3$)$_3$, —$CH_2CH_2$C($CH_2CH_3$)$_3$, —CH($CH_3$)$CH_2$CH($CH_3$)$_2$, —CH($CH_3$)CH($CH_3$)CH($CH_3$)$_2$, and the like.

The term "aryl," alone or in combination refers to an aromatic monocyclic or bicyclic ring system such as phenyl or naphthyl.

When two γ-PNA miniprobes are supplied in a kit each γ-PNA miniprobe may be supplied in a separate receptacle or alternatively, appropriate amounts of both γ-PNA miniprobes can be combined and placed in a single receptacle. Such a kit also will contain a receptacle for the diluent as well as other agents, for example, reducing agents denaturing agents and washing solutions that necessary for labeling telomeric DNA.

Shortening of telomeres is a hallmark of several diseases in humans. A malfunction in telomere maintenance genes, such as due to a mutation in the gene is one reason why telomeres are abruptly shortened in cells. Such a decrease in telomere length results in the onset of several genetically related conditions, exemplary of which without limitation are Dyskeratosis congenita, familial aplastic anemia, familial idiopathic pulmonary fibrosis, Hoyeraal-Hreiderasson syndrome, myelodysplastic syndrome, Revesz syndrome and Coats plus syndrome. Short telomeres are associated with a high risk and a poor prognosis for treatment of the following diseases—pulmonary fibrosis, aplastic anemia, liver disease and fibrosis, various types of cancer, cadiovascular disease, osteoporosis and osteoarthritis, Barrett's esophagus and ulcerative colitis (precursor to cancer) and immune and inflammatory diseases.

Chemical and environmental factors as well as stress are known to cause damage to telomeres. For instance, exposure to chemical and environmental toxins, oxidative stress due to an increase in the intracellular levels of free radicals are known to damage telomeres and trigger associated pathological conditions. Illustrative of diseases and conditions associated with damaged telomeres include without limitation genetic disorders associated with mutations in DNA repair genes, for example, Werner syndrome, gene disorders from exposure to the environmental toxins hexavalent chromium and arsenic, as well as disorders related to poor diet, stress and lack of exercise are some of the pathological conditions that are linked to telomere damage.

γ-PNA miniprobes and chimeric γ-PNA probes of the invention are suitable for detecting short and damaged telomeres in a cell sample. To evaluate whether the inventive γ-PNA miniprobes effectively hybridize to telomeric DNA, a fluorescently labeled γ-PNA miniprobe having 12 PNA monomers (12-mer) was synthesized as described below. This γ-PNA miniprobe consisted of two repeating six residue units, each having a sequence which is complementary to human telomeric DNA. The fluorescent label used for this study was Cy3, which was covalently conjugated at the N-terminus of the γ-PNA miniprobe as illustrated in FIG. 2 (see probe identified as γPNA-1).

FIG. 2 provides the sequences of four γ-PNA miniprobes according to the present invention. Groups underlined in these sequences correspond to PNA monomers having a mini-PEG group as the γ-carbon substituent. Ex-vivo hybridization studies using of the γ-PNA miniprobes (γPNA-1) and two model telomeric DNAs, Telo-2 having two contiguous six residue repeat units and Telo-4 having four contiguous six residue repeat units have illustrated the formation of stable heteroduplex structures with melting temperatures ($T_m$) greater than 75° C. See FIG. 3. As illustrated by the melting temperature curves, the Telo-4/Cy3-PNA-1 hybrid has a higher melting temperature than the Telo-2/Cy3-PNA-1 hybrid indicating that the former hybrid has higher thermal stability than the latter hybrid.

Figure 3:
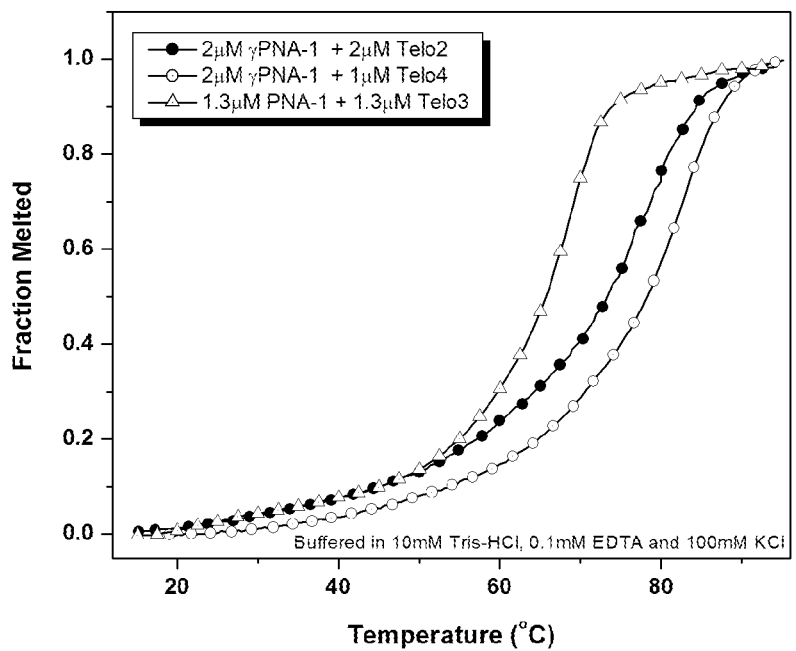
FIG. 3 illustrates the UV melting curves recorded for γPNA-1 and Telo-4 in the presence of 100 mM KCl.

These results are unexpected because they indicate that the shorter γ-PNA miniprobes do not require unwinding of DNA to permit hybridization. Rather, the short γ-PNA miniprobes can bind DNA with secondary structure. Under the experimental conditions used for the hybridization study the four-repeat Telo-4 DNA used in the study has a folded intramolecular guanine quadruplex secondary structure. Yet, the data in FIG. 3 illustrate greater binding of PNA-1 to Telo-4 as compared to Telo-2 indicating that hybridization was not inhibited by the secondary structure of Telo-4.

Figure 4:
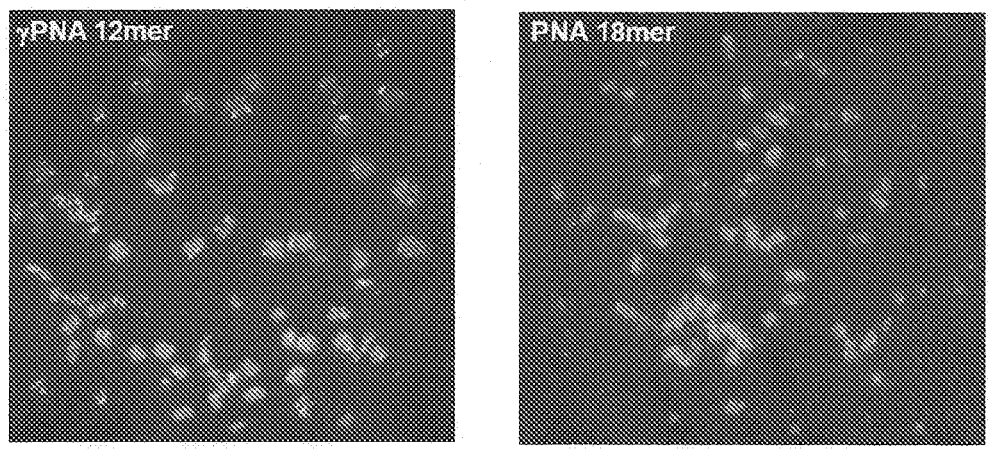
FIG. 4 shows fluorescence micrographs of chromosomal DNA stained with γPNA 12mer (γPNA-1, left) or conventional PNA 18mer (PNA, right). Fluorescence is from DAPI counterstain.

The ability of γ-PNA miniprobes to label telomeres within cells was explored using fixed osteosarcoma cells. For this study, Cy3-labeled γPNA-1, a 12-mer, was introduced into fixed cells under standard conditions used for telomere labeling studies. A conventional Cy3 labeled 18-mer PNA probe was used as a control in this study. As illustrated in FIG. 4, Cy3-γPNA-1 was more efficient at labeling telomeres on most of the chromosomes within the cell sample. Under identical conditions, by contrast, the conventional Cy3-labeled 18-mer PNA probe labeled fewer telomeres. See FIG. 4. This result indicated that the γPNA-1 probe according to the present invention hybridizes telomeric DNA more efficiently that the conventional 18-mer PNA probe.

Figure 5:
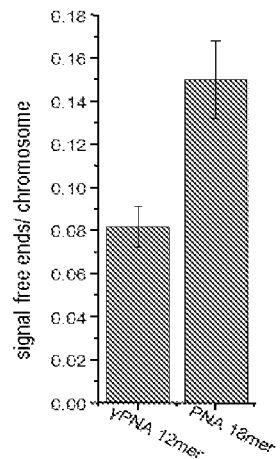
FIG. 5 presents a comparison of signal-free ends in metaphase chromosome spreads stained with γPNA 12mer or conventional PNA 18mer. Data represent means and standard deviations from 10 metaphase spreads.

The present inventors used fluorescent microscopy to quantify the fraction of chromosomes in a cell sample that have not been labeled by a γ-PNA miniprobe of the present invention. In this study, the percent of chromosomes having signal-free (unlabeled) ends after labeling with a γ-PNA miniprobe was compared to the percent of chromosomes having signal-free ends after labeling with a conventional 18-mer PNA probe. As illustrated by the bar graph in FIG. 5, Cy3-γPNA-1 is 45% less likely to fail at hybridizing and staining telomeres than the conventional fluorescently labeled PNA 18-mer used as a control. These results indicated that the inventive γPNA miniprobes are more efficient at labeling shorter telomeres than the conventional fluorescently labeled 18-mer PNA probe. This permits the γPNA miniprobes of the invention to be used as diagnostic biomarker for detecting the risk for the onset or progression of age related diseases and cancer.

The shorter length of the inventive γPNA miniprobes as compared to a conventional 18-mer PNA probe permits a greater number of the former to bind to a telomeric DNA. As a result, a telomere labeled using a γPNA miniprobe is brighter than a telomere labeled using the conventional 18-mer PNA probes. In fact, fluorescent measurement studies by the inventors showed that 50% more fluorescent dye was delivered to the telomere using a γPNA miniprobe than the conventional fluorescently labeled 18-mer PNA. For example, three 12-mer γPNA miniprobes will hybridize to 6 telomere repeats, whereas only two conventional 18-mer PNA probes will hybridize to the same length of telomeric DNA. If it is assumed that the fluorescence quantum yield of the dye is the same for both types of probe, 50% greater signal should be observed for the γPNA miniprobe. For shorter 6mers and/or internally labeled γPNA miniprobes, even more dyes/telomere repeat will be delivered, leading to even brighter signals. The greater concentration of dye resulted in brighter fluorescence which helps to obtain a better image of the telomere and a more accurate quantitative measurement of telomere length and damage.

Figure 6:
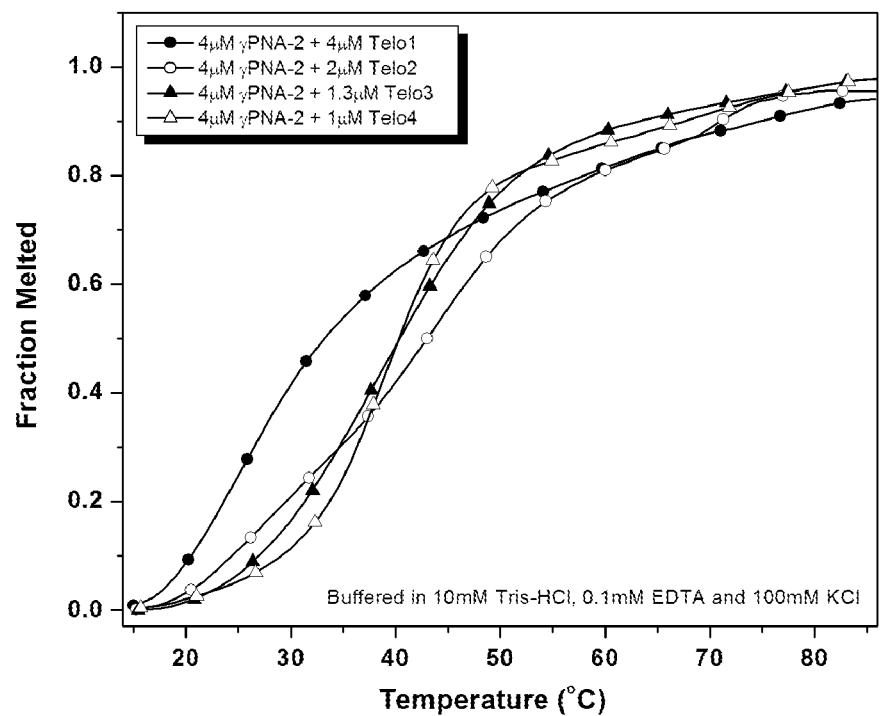
FIG. 6 depicts UV melting curves recorded for γPNA-2 and DNA probes Telo-1-Telo-4.

Brightness of telomere labeling can be further increased by increasing the number of γPNA miniprobes hybridizing to a telomeric DNA. This was shown by synthesizing a six residue γPNA miniprobe (γPNA-2). As illustrated in FIG. 6, UV melting curves demonstrated that γPNA-2 hybridizes to each of the four model telomeric DNA targets, Telo-1, Telo-2, Telo-3 and Telo-4 having one, two, three and four repeat units respectively with differing affinities. Hybridization of the γPNA miniprobe to telomeric DNA was cooperative as reflected by an increase in the steepness of the melting point curve as the number of repeat units in the telomere increased from one to four. See FIG. 6. The phrase "cooperativity of hybridization" and the term "cooperativity" refer to a special case of allostery involving hybridization of two DNA strands, hybridization of a DNA to an RNA, hybridization of a DNA to a PNA (modified or unmodified), hybridization of an RNA to a PNA (modified or unmodified), or hybridization of PNA strands such that hybridization of a first PNA molecule, such as a γPNA miniprobe or a chimeric γPNA probe to telomeric DNA promotes hybridization of subsequent PNA molecules to the DNA.

FIG. 6 showed that the curve representative of hybridization between a γPNA miniprobe and a telomeric DNA having two six residue repeats had a steeper central or transition region that the curve associated with the hybridization of a γPNA miniprobe to telomeric DNA having a single six residue repeat. A further increase in the number of repeat units in the telomeric DNA was expected to enhance cooperativity of hybridization and as illustrated by FIG. 6 melting curves for the Telo-3-γPNA-2-Cy3 hybrid and the Telo-4-γPNA-2-Cy3 hybrid had a steeper and more well defined transition or central region that the melting curves for the two repeat hybrid (Telo-2-γPNA-2-Cy3).

Figure 7:
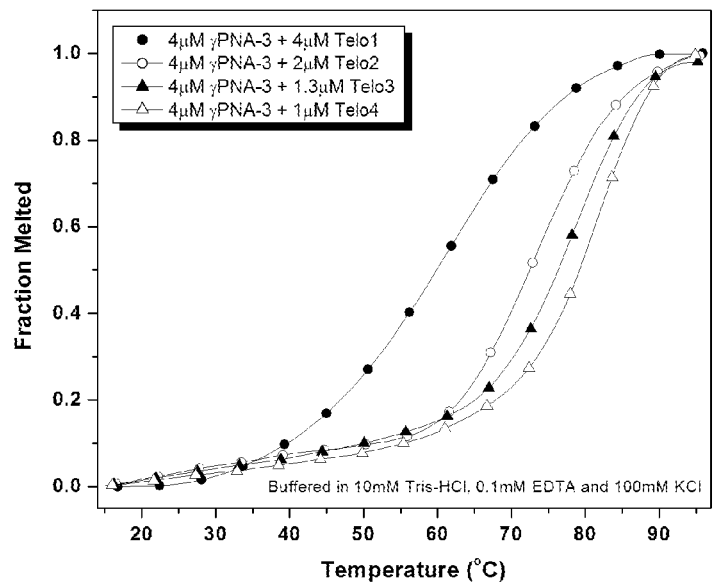
FIG. 7 presents UV melting curves recorded for G-clamp miniprobe γPNA-3 and DNA probes Telo-1-Telo-4.

Binding of the inventive γPNA miniprobe to telomeric DNA was found to increase the thermal stability of the hybrid. For instance, as shown in FIGS. 6 and 7, the melting points of γPNA miniprobe-telomeric DNA hybrids increased as the number of repeat units in the telomeric DNA increased. The present inventors believe this increase in thermal stability to be due to greater end-stacking interactions in the γPNA miniprobe-telomere hybrid when a large number of γPNA miniprobes hybridize adjacent to each other on telomeric DNA. Even though the two miniprobes are not covalently linked, in such as hybrid the aromatic base from the end of one probe pi-stack with the aromatic base from the end of the adjacent probe, analogous to base stacking within a continuous helix.

While a six residue γPNA miniprobe (PNA-2) was observed to form a stable heteroduplex with telomeric DNA in solution, PNA-2 failed to adequately stain telomeres in fixed cells. The lack of telomere staining activity for the 6-mer is attributed to be due to lower thermodynamic stability of the hybrid of PNA-2 and telomeric DNA. This lower thermodynamic stability is thought to translate to a greater rate of de-hybridization of the 6-mer, PNA-2 as compared to the longer 12-mer (PNA-1) described above.

To enhance the telomere staining activity of the shorter six residue γPNA-2, the present inventors replaced two of the three cytosine bases in γPNA-2 (see FIG. 2) with a modified cytosine unit termed a "G-clamp," shown in FIG. 1. This modified base features a larger pi-stacking surface in addition to an appendage that permits additional hydrogen bonding interactions when paired with guanine, essentially clamping the complementary guanine residue.

Figure 8:
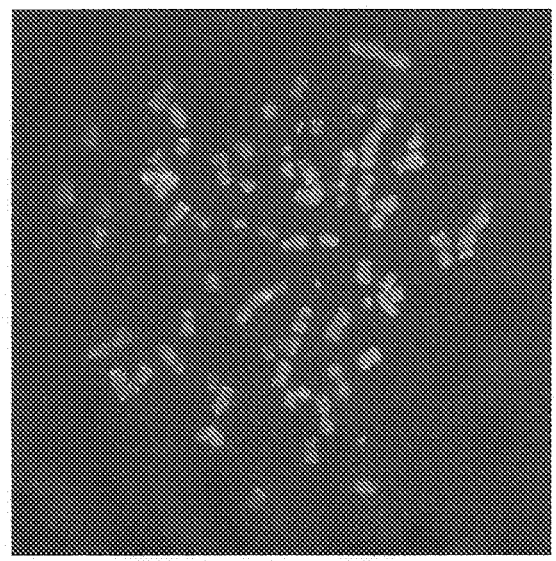
FIG. 8 shows a fluorescence micrograph of chromosomal DNA stained with G-clamp γPNA 6mer (γPNA-3).

The inventors observed that replacing one or more cytosine residues in PNA-2 with a G-clamp residue, as illustrated by the hexamer miniprobe γPNA-3 in FIG. 2, increased the thermal stability of the hybrid. Hybridization studies involving Cy3 end labeled γPNA-3 and the four telomeric DNA targets Telo-1, Telo-2, Telo-3 and Telo-4 have indicated a greater thermal stability for the G-clamped PNA miniprobe. In fact, its clear from FIGS. 6 and 7, that the melting point of a G-clamped Cy3-γPNA-3 miniprobe-Telo-1 hybrid was greater than the melting point of a six residue Cy3-γPNA-2 miniprobe-Telo-1 hybrid. This increase in thermal stability extends to hybrids formed between the G-clamped Cy3-γPNA-3 miniprobe and telomeric DNA having two, three and four sequence repeats. See FIG. 7. In fact, as shown by the image in FIG. 8, the G-clamped Cy3 labeled γPNA-3 miniprobe was at least if not more efficient than the 12-residue PNA-1 miniprobe at labeling telomeres.

Using shorter γ-PNA miniprobes for labeling telomeres in cells has certain advantages. Since telomeres consist of a repeating 6-base sequence, more copies of the six residue γPNA miniprobe can bind adjacent to each other on the complementary telomere strand. That is, decreasing the length of the γ-PNA miniprobe to six residues corresponding to a single repeat of the telomere permits three times as many labels, for example a fluorescent dye, to concentrate on the telomere as compared to a labeled conventional 18 mer PNA probe. See FIG. 9A Increasing the number of labeled γ-PNA miniprobes translates, therefore, to a higher concentration of the detectable label and thus a brighter image of the telomeres. As a result, when the inventive γ-PNA miniprobes are used in diagnostic assays, the increased intensity of detectable signal should provide greater sensitivity of detection and consequently a lower the error associated with the measurement of telomere length or visualization of damage that has occurred to telomeres in a cell sample. The inventive shorter γ-PNA miniprobes also permit the detection of short telomeres that are implicated to play a role in pathological processes, thereby improving the early detection of such diseases.

Accordingly, the present inventors have tested the ability of a nine γ-PNA miniprobe (9-mer) to detect telomeric DNA. A 9-mer hybridizes 1.5 repeat units of a telomere. Thus, two γPNA miniprobes having different sequence specificities are to be used for telomere detection according to this methodology. The sequences of the two γPNA miniprobes were designed to permit the miniprobes to hybridize at adjacent positions along a DNA telomere. Each γ-PNA miniprobe was functionalized using a different dye, such that one γ-PNA miniprobe contains the donor dye that acts as the light absorber and will donate the absorbed energy to the acceptor dye on the other γ-PNA miniprobe by Förster Resonance Energy Transfer (FRET).

Figure 13:
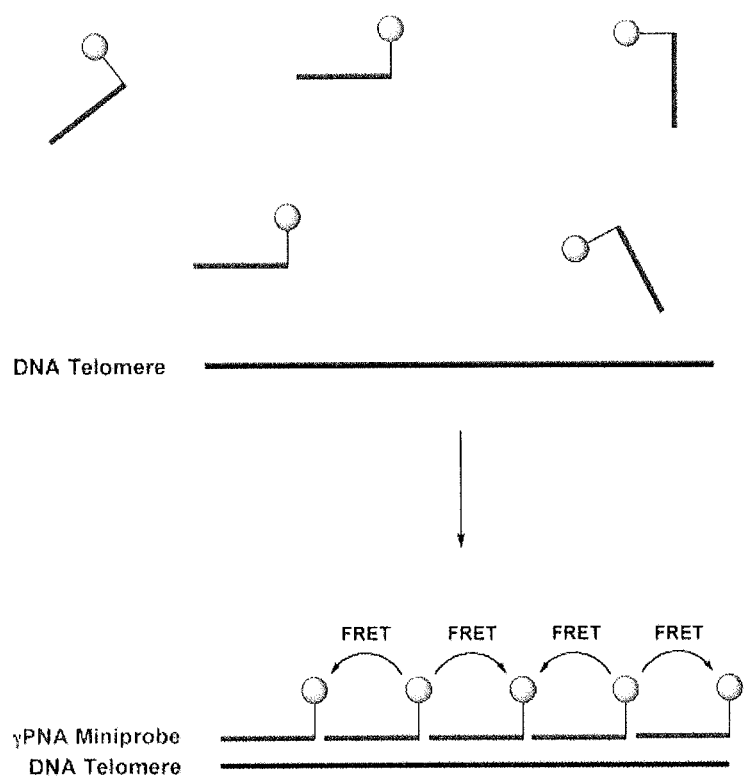
FIG. 13 is an illustration of "Scheme 1," depicting how the shorter γ-PNA miniprobes of the invention permit donor and acceptor dyes to be close to each other, which in turn permits efficient FRET which improves telomere detection.

The efficiency of FRET decreases as the sixth power of the distance between the donor and acceptor dyes ($r^{-6}$). Accordingly, conventional PNA telomere probes, which are 18 bases in length, will not exhibit efficient FRET in the format depicted in Scheme 1 (FIG. 13), since the donor and acceptor dyes are approximately 64 Å apart. The shorter γ-PNA miniprobe of the invention permits the donor and acceptor dyes to be close to each other. This permits efficient FRET which improves telemore detection.

Experiments by the present inventors have confirmed a greater efficiency of FRET using two 9mer γ-PNA miniprobes for labeling telomeric DNA. FRET based detection was enhanced because of the shorter distance between the donor and acceptor dyes, approximately 32 Å when the inventive 9-mers were used. FRET efficiency was approximately 75% when fluorescein is used as the donor and Cy3 is used as the acceptor.

The advantage of using FRET in a detection assay of the invention as described in Scheme 1 (FIG. 13), is to prevent background fluorescent signal from interfering with telomere detection. Because the acceptor dye in a donor-acceptor FRET pair fluoresces at longer wavelength than the donor dye, any fluorescence due to unhybridized miniprobes will be at the shorter wavelength corresponding to the wavelength at which the donor dye fluoresces. By employing appropriate filters, moreover, unwanted short wavelength fluorescence can be removed so as to permit only the stained telomeres to be imaged. Accordingly, the inventive method eliminates time-consuming washing steps normally associated with fluorescence in situ hybridization (FISH) experiments.

Figure 14:
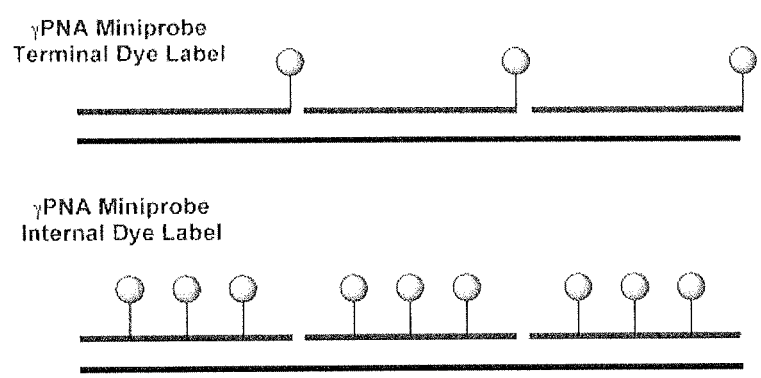
FIG. 14 is an illustration of "Scheme 2," depicting how multiple labels can be covalently attached to a single domain of the inventive γ-PNA miniprobe.

As described above the multiple labels can be covalently attached to a single domain of the inventive γ-PNA miniprobe, as illustrated in Scheme 2 (FIG. 14).

According to the method illustrated in Scheme 2 (FIG. 14), each γ-PNA miniprobe will have between one and four dye molecules. The dyes will be conjugated to one or both of the end PNA monomers and/or to one or more internal PNA monomers of the γ-PNA miniprobe of the present invention. The advantage of conjugating multiple dye molecules to each γ-PNA miniprobe is that each miniprobe delivers more dye to a given length of the telomeric DNA than is possible using a single dye γ-PNA miniprobe.

For example, if a 12-mer γPNA miniprobe is internally labeled at 3 positions rather than at one position then such a miniprobe will deliver three times more dye than a single dye probe, essentially tripling the brightness of fluorescence as long as self-quenching of the dyes is avoided. Conjugation of the dyes to the γPNA miniprobe will proceed via the functionalization of a cytosine (C), thymine (T), or a uracil (U) nucleobase as reported by Gierlich et al., *Org. Lett.*

2006, 8, 3639-42. The dye can also be attached to the PNA backbone via backbone functionalization using a mini-PEG group at the γ-carbon of the PNA. The concept of conjugating multiple molecules of a single dye to a γPNA miniprobe can be extended to a FRET based detection system by using alternating donor and acceptor dyes to maximize the FRET signal.

Figure 15:
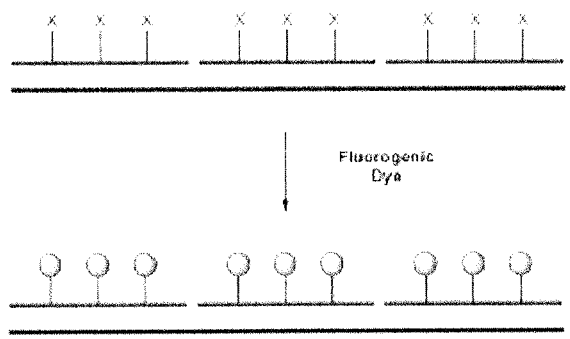
FIG. 15 is an illustration of "Scheme 3," depicting a γ-PNA miniprobe functionalized with one or more reactive groups (X) at an internal and/or terminal position and subsequently labeled with a fluorogenic dye.

The use of internally labeled γPNA miniprobes can be further expanded to detect hybridization efficiency. Accordingly, as illustrated in Scheme 3 (FIG. 15), a γPNA miniprobe will be functionalized with one or more reactive groups (X) at an internal and/or terminal position. After hybridization to a target DNA, such as telomeric DNA, the unbound probe will be removed through the use of standard washing steps. A dye that is functionalized to form a covalent bond to the probe will then be added to the telomeric DNA-γPNA miniprobe hybrid to cause fluorescent labeling of the telomeric DNA. An advantage of this methodology is that a single probe can be used to form the telomeric DNA-γPNA miniprobe hybrid, but detection can be enhanced by using a variety of dyes to obtain fluorescence in a range of colors.

According to this method fluorescent labeling of the telomere will occur when a fluorogenic compound, for example, a non-fluorescing dye reacts with a functionalized γPNA miniprobe to form a fluorescent product. The use of a fluorogenic dye is advantageous since it does not require removal of the unbound dye prior to imaging. The elimination of such washing steps cut down the experimental time making the inventive method cost effective.

According to one aspect of this methodology, a 3-azido coumarin will be used as the fluorogenic dye and the γPNA miniprobe used will be functionalized to bear a terminal alkyne group. The reactive alkyne group on the γPNA miniprobe can be attached to the backbone via the miniPEG substituent or alternatively, the reactive alkyne group may be present on a nucleobase. The labeling of telomeric DNA according to this methodology is illustrated in Scheme 4, where an alkyne functionalized γPNA miniprobe will be permitted to contact an azido dye under mild conditions to form a triazole linked dye-γPNA miniprobe product that is fluorescent.

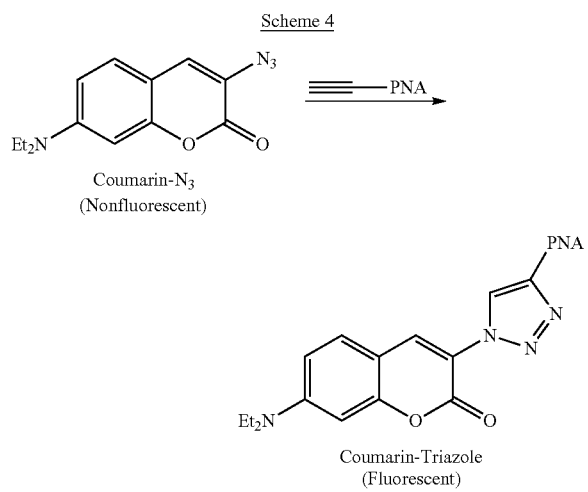

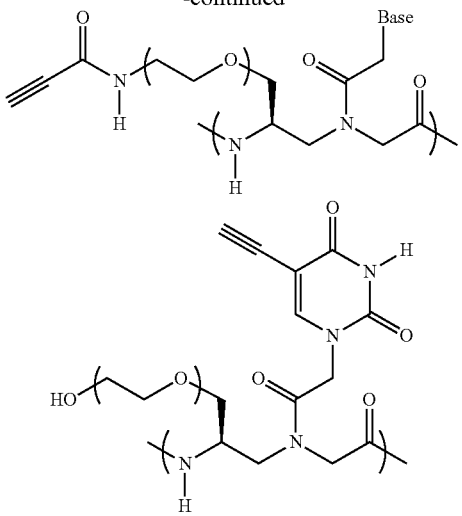

Figure 9:
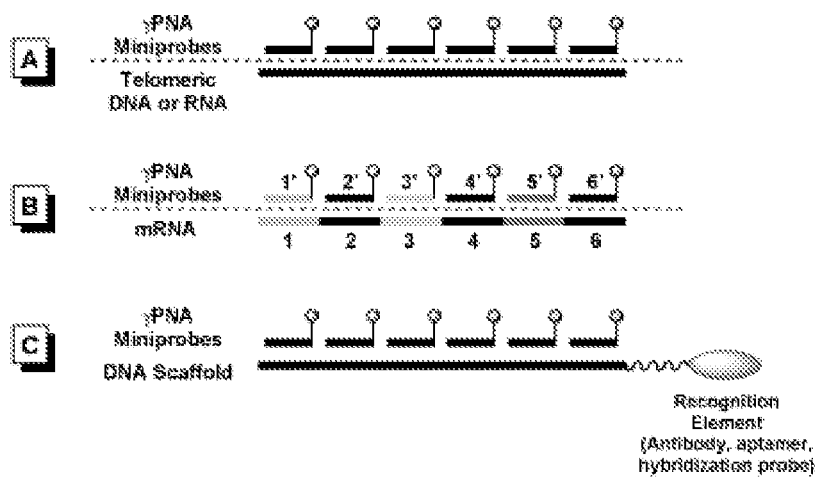
FIG. 9 illustrates three formats for using γPNA miniprobes for bright fluorescent labeling of nucleic acid, protein, or other targets.

While the description above relates to the use of γ-PNA miniprobes to detect and visualize telomeric DNA, a similar strategy also can be applied for targeting other regions of genomic DNA where repetitive sequence elements are found, such as centromeres or microsatellite DNA, or sequences involved in triplet repeat disorders such as Huntington's disease or Fragile X syndrome. Moreover, by generating libraries of γ-PNA miniprobes it is possible to extend the inventive technology to detect and image a non-repetitive (mixed) DNA or RNA sequence. The γPNA miniprobes described above also can be used to detect telomeric RNA (TERRA) via an RNA FISH assay. According to another embodiment, a library of γPNA miniprobes will be designed such that the individual miniprobes assemble cooperatively on a mixed sequence template, such as an mRNA (FIG. 9B).

The present technology can be further expanded to construct nanostructures of the inventive γ-PNA miniprobes, such as fluorescent nanotags. Thus, a γPNA miniprobe based nanostructure would be employed as a nanotag for binding to a DNA scaffold that has a repeating sequence, to which scaffold is covalently conjugated a recognition element such as an antibody, an aptamer or a hybridization probe, as shown in FIG. 9C. By assembling several such nanotags on the DNA scaffold a bright fluorescent label for staining DNA, proteins or other target molecules is obtained.

Chimeric γPNA Probes for Enhanced Specificity

The invention also contemplates chimeric γ-PNA probes for detecting cellular RNA or DNA, such as telomeric DNA. The chimeric γ-PNA probes of the invention are designed to improve specificity of hybridization by using two domains that will have γ-PNA monomers of opposite chirality. The term "chirality," here refers to the ability of one or more γPNA monomers to induce a right-handed or a left-handed twist (helicity) to the γPNA helix. For instance, an R-configuration γ-minipeg monomer will induce a right-handed helical chirality in a given domain, while the L-enantiomer will induce left-handed helical chirality.

By using both right-handed and left-handed mini-PEG γ-PNA monomers the present inventors will synthesize a chimeric γPNA probe having a right-handed domain and a left-handed domain that are attached to each other end-to end. The right-handed domain will have a sequence that is complementary to the sequence of a target DNA, such as telomeric DNA and will contain at least four PNA residues.

Typically, the right-handed domain will contain between 4-10 PNA monomers with at least one of the PNA monomers being a γ-PNA monomer. Thus, the right-handed domain can contain four PNA monomers, five PNA monomers, six PNA monomers, seven PNA monomers, eight PNA monomer, nine PNA monomers or ten PNA monomers.

Extending from one end of the right-handed domain is the second domain made exclusively from left-handed PNA monomers. The sequence of the left-handed domain will be chosen so as to prevent this domain from hybridizing to the target RNA or DNA, such as a telomeric DNA in a biological sample. The left-handed domain will have at least four PNA monomers, for example, between 4-7 PNA monomers. Thus, the left-handed domain can contain five PNA monomers, six PNA monomers or seven PNA monomers with at least one of the PNA monomers in the left-handed domain being a γ-PNA monomer. The right-handed and left-handed domains can be directly attached end-to-end via an amide bond or the two domains are attached using a linker. The category "linker" refers to a ($C_1$-$C_{10}$) alkylene, a ($C_3$-$C_{14}$) arylene-($C_1$-$C_{10}$) alkylene, ($C_1$-$C_{10}$) alkylene-O—($C_1$-$C_{10}$) alkylene, or a ($C_1$-$C_{10}$) alkylene-S—($C_1$-$C_{10}$) alkylene residue.

In the present context, the term "alkylene" refers to divalent alkyl and divalent substituted alkyl, respectively. Examples of alkylene include without limitation, ethylene (—$CH_2$—$CH_2$—). "Optionally substituted alkylene" refers to alkylene or substituted alkylene.

"Arylene" denotes divalent aryl, and "substituted arylene" refers to divalent substituted aryl. "Optionally substituted arylene" refers to arylene or substituted arylene.

The detection of telomeric DNA using the chimeric γ-PNA probes will proceed by providing an equimolar mixture of two chimeric γPNA probes. According to the inventive method, the right-handed domain of the second chimeric γPNA probe will have a sequence that targets a site on the telomeric DNA that is in close proximity to the right-handed domain of the first chimeric γPNA probe. Thus, the right-handed domains of the first and second chimeric γPNA probes can bind adjacent residues of a telomeric DNA. Alternatively, there may be a gap of 1-3 residues between the first and second chimeric γPNA probes. Thus, the right-handed domains of the first and second chimeric γPNA probes bind so as to have 0, 1, 2 or 3 unhybridized telomeric DNA residues between the first and second chimeric γPNA probes.

Figure 10:
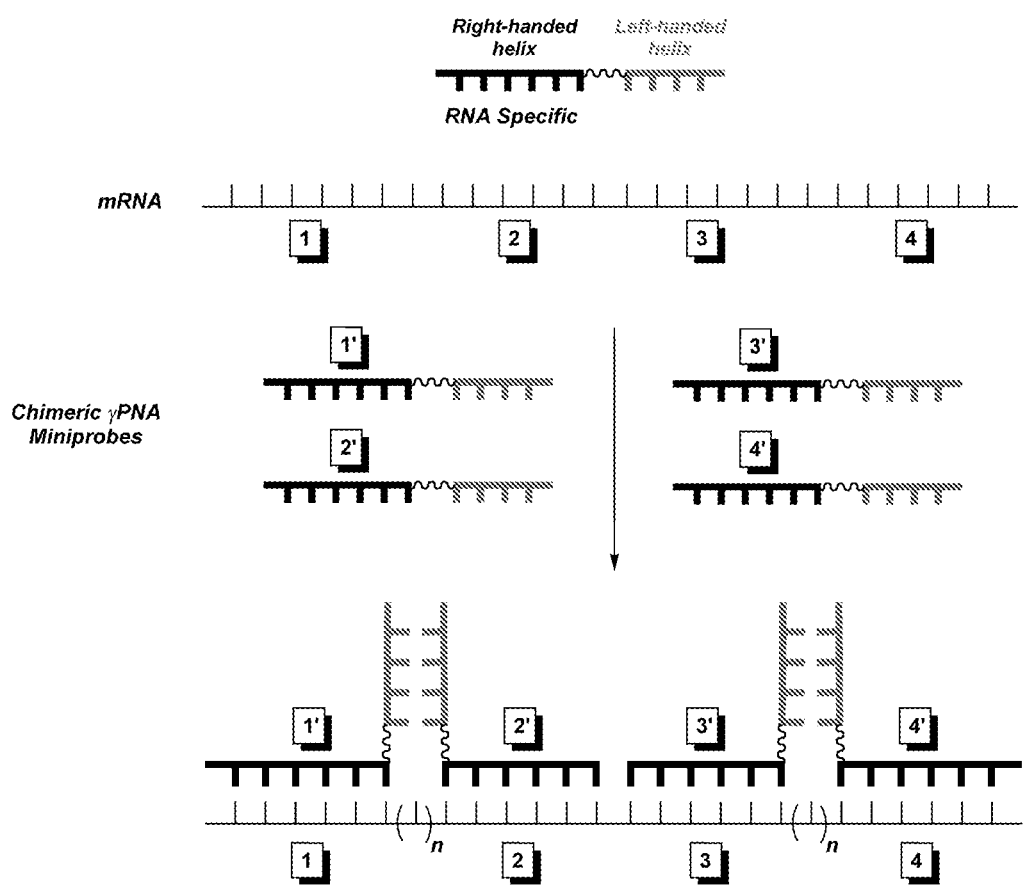
FIG. 10 depicts the hybridization of a chimeric γPNA probe to a telomeric DNA.

As illustrated in FIG. 10, the left-handed domain of the second chimeric γPNA probe will have a sequence that is complementary to the sequence of the left-handed domain of the first chimeric γPNA probe. Hybridization of the two probes to the telomeric DNA will permit their respective left-handed domains to hybridize which provides additional stability to the ternary complex of the chimeric probe with telomeric DNA or a cellular RNA target of interest. The advantage of this approach is that it uses few PNA monomers to synthesize each domain of the chimeric γPNA probe but greatly enhances specificity of hybridization.

Figure 11:
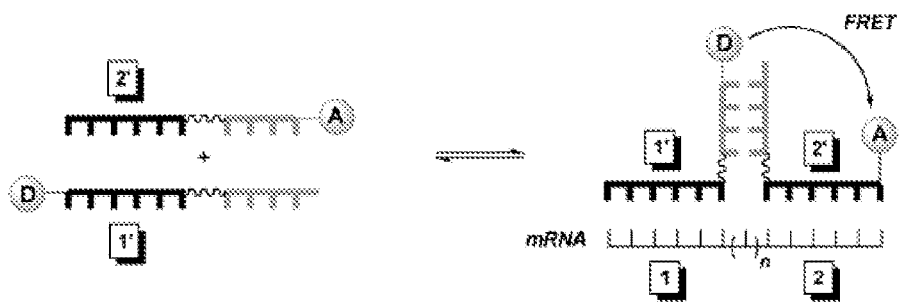
FIG. 11 and FIG. 12 respectively illustrate FRET-based detection of telomeric DNA, using different types of chimeric γPNA probes.

The chimeric γPNA probe described above thus delineates a new class of fluorescence in-situ hybridization (FISH) reagent. As shown in FIG. 11, two adjacent probes can be functionalized using donor and acceptor dyes for FRET-based detection of telomeres. While the donor or acceptor dyes are shown to be covalently attached to a terminal PNA residue of the chimeric γPNA probe, these dyes can also be covalently linked tointernal PNA residues. Nucleobases such as uracil or cytosine can be used to covalently link the donor-acceptor dyes that form the FRET pair, as shown below, or the donor-acceptor dyes can be covalently linked to the end of the mini-PEG group of a γPNA.

The advantage of using a chimeric γPNA probe for detecting telomeric DNA is that the two dyes are brought in proximity by virtue of the sequences of the first and second chimeric γPNA probes, so as to permit efficient FRET. Because the donor and acceptor dyes are attached to two separate chimeric γPNA probes, the binding of a single probe to an off-target site, or the remnants of dye in unhybridized probes will have no effect on the measured FRET signal.

Figure 12:
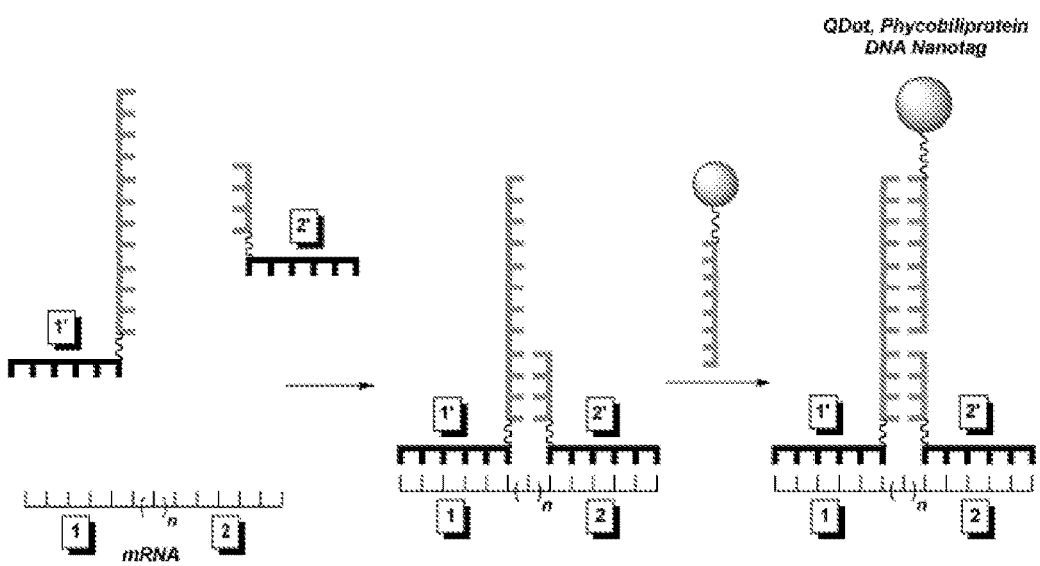

The methodology of the invention can be expanded to include post-hybridization labeling of the RNA or telomeric DNA as illustrated in FIG. 12. Here, two chimeric γPNA probes having different lengths with respect to each other are utilized for detection of telomeric DNA. According to this approach, the left-handed domain of a first chimeric γPNA probe will be significantly longer than the corresponding left-handed domain of a second adjacent chimeric γPNA probe. The result will be an overhang of unhybridized PNA residues in the left-handed domain of the first chimeric γPNA probe. To capture overhang and label the RNA or a telomeric DNA in a cell sample, one can employ a γPNA miniprobe, a fluorophore such as a quantum dot, phycobiliprotein, a DNA nanotag, an antibody, streptavidin, or an enzyme that is functionalized with a γPNA miniprobe the sequence of which is complementary to the left-handed domain of the first probe. The overhang capture detection methodology described above can be expanded to the tyramide signal amplification strategy. See Speel, E. J., et al., *J. Histochem. Cytochem.* 1999, 47, 281-88. Accordingly, a γPNA miniprobe or a chimeric γPNA probe will be biotinylated and then permitted to hybridize to a telomeric DNA or cellular RNA. Following hybridization unbound probe is washed away. A streptavidin-horseradish peroxidase (HRP) conjugate will then be contacted with the hybrid, followed by washing to remove unbound streptavidin-HRP conjugate and the addition of a dye-tyramide conjugate. Labeling of a telomeric DNA or a cellular RNA proceeds upon the activation of the dye-tyramide conjugate by hydrogen peroxide. Alternatively, a γPNA-HRP conjugate can be synthesized and used in place of the biotynylated γPNA miniprobe or chimeric γPNA probe mentioned above. A γPNA-HRP conjugate of the present invention can be synthesized using a protocol analogous to the one described by Schönhuber, W., et al., *Appl. Env. Microbiol.* 1997, 63, 3268-73.

EXPERIMENTAL

Materials

PNA oligomers were synthesized and purified according to published procedures. For example, see Christensen, L., et al., *J. Pept. Sci.* 1995, 3, 175-83. Mini-PEG γ PNA monomers were synthesized according to the synthetic protocols described in PCT publication No. WO2012-138955.

UV Melting Curves.

Samples were prepared in buffer containing 10 mM Tris-HCl, 0.1 mM EDTA and 100 mm KCl, pH=7. The concentration of a γ-PNA miniprobe or a chimeric γ-PNA probe is 4 μM. Telomeric DNA used as the template is also present at a concentration of 4 μM.

The concentrations of γ-PNA miniprobes and DNA targets used in the hybridization studies were designed to ensure that the concentration of 6 base repeat sequences was kept constant at 4 μM. For example, the 12mer miniprobe γPNA-1 was used at 2 μM because it has two 6-base repeats, so the concentration of 6 base γPNA-1 repeats was 4 μM. Meanwhile, the 6mer miniprobes γPNA-2 and γPNA-3 were used at 4 μM because they each have a single 6-base repeat.

The γ-PNA miniprobes were mixed with 4 μM Telo-1, 2 μM Telo-2, 1.3 μM Telo-3 or 1 μM Telo-4 for the hybridization study. Melting curves were recorded by monitoring absorbance at 260 nm with heating/cooling ramps of 1° C./min.

Cell Lines and Culture Conditions

U2OS human osteosarcoma cells containing a hygromycin resistant gene were obtained from ATCC and cultured in Dulbecco's Modified Eagle Media, 10% Fetal Bovine Serum, 50 U/mL of Penicillin, and 50 μg/mL of Streptomycin. Cells are grown at 37° C., 5% $CO_2$, and 5% $O_2$ under humid conditions.

Telomere Fluorescent In-Situ Hybridization (Telo-FISH)

For staining and imaging of chromosome metaphase spreads the cells were treated with 0.05 μg/mL colcemid for 16 hours. Cells were subsequently trypsinized, harvested and treated with 75 mM KCl hypotonic buffer for 12 min at 37° C., then fixed and stored in methanol/acetic acid fixing solution (3:1). The fixed cells were dropped onto slides and dried at 70° C. for 3 minutes to spread the chromosomes followed by drying of the cells overnight. The slides were then fixed using 4% formaldehyde to bond the chromosomes to the slides, and treated with 0.1% pepsin in 0.01N HCl for 10 minutes at 37° C.

The fixation and washing step was repeated. The fixed cells were dehydrated by dipping the slides for 5 minutes in a solution of 70%, ethanol, followed by dipping for 5 minutes in 90% ethanol and finally dipping the slide for 5 minutes in 100% ethanol. The slide was air dried after dipping the slide in the last ethanol solution. The chromosomal DNA samples stained with G-clamp γPNA 6mer (γPNA-3) (FIG. 8) were treated with 500 μg/mL RNAse A (Invitrogen) at 37° C. for 10 minutes, rinsed with PBS buffer and then dehydrated again as described above. For all PNA stainings, following a final denaturation step whereby the DNA on the slide are heated at 70° C. for 3 minutes, hybridization to the appropriate Cy3 labeled γ-PNA was carried out using a hybridization mixture containing 70% deionized formamide, 10% NEN blocking reagent [Roche], 0.1 M Tris-HCl [pH=7.4], $MgCl_2$ buffer [82 mM $NaH_2PO_4$, 9 mM citric acid, 20 mM $MgCl_2$], and 0.5 mg/ml of the indicated PNA.

After 2 hours hybridization at room temperature, the slides were washed twice with washing solution I (70% deionized formamide and 10 mM Tris-HCl [pH=7.4]) and three times with wash solution II (70 mM Tris-Cl [pH=7.4], 0.1M NaCl, 0.067% Tween 20), prior to counterstaining with DAPI. The images of metaphase chromosomal DNA were obtained using a Nikon Ti90 epi-fluorescence microscope equipped with PlanApo 60×/1.40 oil immersion objective. The NIS element advanced software was used to acquire and analyze the images with the same settings for chromosomal DNA stained with the γPNA 12mer compared to the PNA 18mer. In order to rigorously identify and quantify telomere staining and telomere signal free (SFE) chromosome ends a series of nine z-stacked images (0.25 μm steps) are acquired for each metaphase chromosomal DNA sample and analyzed. This technique allows for rigorous distinction of a telomere that is unlabeled from a telomere that is labeled but out of focus. The number of SFEs per chromosome is calculated for each metaphase chromosomal DNA sample, and the mean and standard error is determined for chromosomes stained with the γPNA 12mer or the PNA 18mer.

Synthesis

A. Synthesis of Internally Labeled γ-PNA Conjugates

The conjugation of a dye to a monomer of the inventive γ-PNA miniprobe was accomplished by functionalizing a uracil or cytosine nucleobase at carbon 5. Scheme 5 illustrates a C-5 dye conjugated uracil group.

Scheme 5

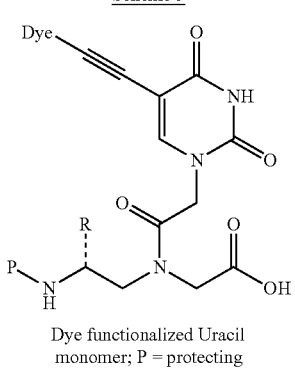

Dye functionalized Uracil monomer; P = protecting group

In an illustrative synthesis coumarin was used as the dye (Scheme 6). More specifically, the conjugation of coumarin to uracil was performed by contacting an iodo-ethyne modified uracil with a coumarin azide under Sonogashira coupling conditions to yield a coumarin-functionalized monomer.

Scheme 6

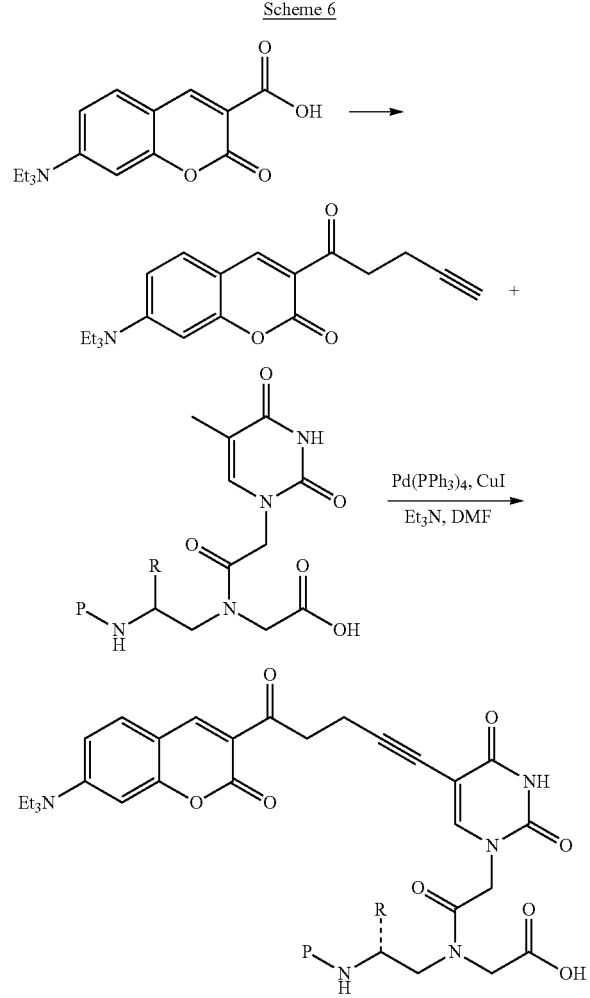

Dye functionalized Uracil monomer; P = protecting group

The coumarin-labeled monomer then will be used for the synthesis of a γ-PNA miniprobe or a chimeric γ-PNA probe according to the present invention. See Dragulescu-Andrasi, A. et al *J. Am. Chem. Soc.* 2006, 128, 10258-67. Table 1 shows the results of a fluorescence intensity study using unmodified internally labeled PNA probes. The residues in bold underlined in Table 1 illustrate the position of the coumarin dye in these sequences. Each PNA probe shown in Table 1 contained two coumarin dyes. These PNA probes were hybridized to a complementary DNA. The fluorescence intensity of the resultant hybrid was measured and compared to the fluorescence intensity of an equimolar amount of coumarin acid used as a control. As illustrated by the data in Table 1 the position of the labeled monomer within the PNA oligomer does not influence hybridization to DNA, since the relative fluorescence values for each of the PNA-DNA hybrids is about the same. The fluorescence of the PNA-DNA duplexes, moreover, was not quenched due to the two internally-labeled PNA monomers. See Table 1.

TABLE 1

| PNA | Sequence | Relative Fluorescence[a] |
|---|---|---|
| I | H₂NLys-CGATTTCGA-H (SEQ ID NO: 1) | 2.1 |
| II | H₂NLys-CGATTTTCGA-H (SEQ ID NO: 1) | 2.0 |
| III | H₂NLys-CGATTTCGA-H Coumarin Acid (SEQ ID NO: 1) | 1.8<br>1.0 |

[a]The coumarin-labeled PNAs were allowed to hybridize with a complementary DNA oligonucleotide. The fluorescent intensities of each hybrid was measured and compared to the fluorescent intensity of coumarin acid alone to obtain the relative fluorescence. The site of coumarin incorporation is shown by bold underline.

In fact, the relative fluorescence for the hybrid with the PNA probe, having two coumarin-labeled PNA monomers directly adjacent one another (PNA-III), was only slightly lower (i.e., quenched by 10-15%) than the relative fluorescence for the hybrid obtained using the PNA oligomer in which the two coumarin-labeled PNA monomers are separated by two unlabeled bases. Without ascribing to a particular hypothesis, the present inventors believe that very little fluorescence quenching was observed in the PNA-telomeric DNA hybrid systems described above because of the relatively short and rigid linker used to conjugate the dye to the uracil or cytosine nucleobases. These results point the way to using coumarin labeled, multi dye-containing γ-PNA miniprobes in fluorescence intensity studies.

What is claimed is:

1. A kit for detecting a telomeric DNA in a cell sample, comprising (A) a receptacle that contains a mini-PEG modified γPNA miniprobe that hybridizes with the telomeric DNA, and (B) a receptacle that contains a diluent suitable for hybridization, wherein the mini-PEG modified γPNA miniprobe comprises at least one PNA monomer that is a mini-PEG modified γPNA monomer having the structure

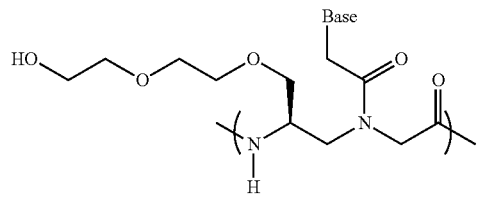

wherein Base is a nucleobase.

2. The kit according to claim 1, wherein the mini-PEG modified γPNA miniprobe consists of six, nine or twelve PNA monomers.

3. The kit according to claim 1, wherein the mini-PEG modified γPNA miniprobe comprises at least one fluorescent dye as a detectable label.

4. The kit according to claim 3, wherein the fluorescent dye is selected from the group consisting of Cy3, Cy3B, Cy3.5, Cy5, Cy5.5, Cy7, coumarin, acridine derivatives, eosin derivatives and fluorescein.

5. The kit according to claim 3, wherein the detectable label is attached to a N-terminal or a C-terminal PNA monomer or a N-terminal or a C-terminal γPNA monomer of the mini-PEG modified γPNA miniprobe.

6. The kit according to claim 3, wherein the detectable label is attached to an internal PNA monomer or an internal γPNA monomer of the mini-PEG modified γPNA miniprobe.

7. The kit according to claim 3, wherein the detectable label is attached to a uracil or a cytosine nucleobase of a PNA monomer.

8. The kit according to claim 6, wherein the detectable label is attached to a γ-carbon of the γPNA monomer.

9. The kit according to claim 8, wherein the detectable label is attached to the γ-carbon of the γPNA monomer via a linker $CH_2—(O—CH_2—CH_2)_n—X$, wherein X is selected from the group consisting of $—NH_2$, $—CH=CH—$, $—COOH$ and $—N_3$ and n is an integer from 1 to 10.

10. The kit according to claim 1, wherein the mini-PEG modified γPNA miniprobe comprises two fluorescent dyes.

11. The kit according to claim 1, wherein the nucleobase sequence of the mini-PEG modified γPNA miniprobe consists of:

(A) CCCTAA (nucleobases 13-18 of SEQ ID NO: 2), wherein at least one C is replaced with a G-clamp nucleobase;

(B) CCCTAACCC (nucleobases 10-18 of SEQ ID NO: 2); or (C) CCCTAACCCTAA (nucleobases 7-18 of SEQ ID NO: 2).

12. A chimeric mini-PEG modified γPNA miniprobe, comprising:

(i) at least one PNA monomer that is a mini-PEG modified γPNA monomer having the structure

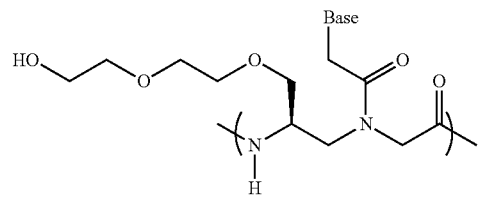

wherein Base is a nucleobase;

(ii) a first, right-handed, domain comprising right-handed PNA monomers, and (iii) a second, left-handed, domain comprising left-handed PNA monomers, wherein the first and second domains are attached to each other end-to-end, optionally via a linker.

13. The chimeric mini-PEG modified γPNA miniprobe according to claim 12, wherein (A) the first domain comprises from 4 to 10 right-handed PNA monomers; and (B) the second domain comprises from 4 to 7 left handed PNA monomers.

14. The chimeric mini-PEG modified γPNA miniprobe according to claim 12, wherein the sequence of the first domain is complementary to a telomeric DNA and the second domain does not hybridize with the telomeric DNA.

15. The chimeric mini-PEG modified γPNA miniprobe according to claim 14, wherein the first domain comprises nine right-handed γPNA monomers and the second domain comprises six left-handed γPNA monomers.

16. The chimeric mini-PEG modified γPNA miniprobe of claim 12, further comprising at least one detectable label covalently attached to the first domain or the second domain.

17. The chimeric mini-PEG modified γPNA miniprobe of claim 12, wherein the first domain is attached to the second domain via a linker.

18. The chimeric mini-PEG modified γPNA miniprobe of claim 12, further comprising at least one detectable label covalently attached to the first domain or the second domain, wherein the first domain is attached to the second domain via a linker.

19. A mini-PEG modified γPNA miniprobe comprising at least one PNA monomer that is a mini-PEG modified γPNA monomer having structure:

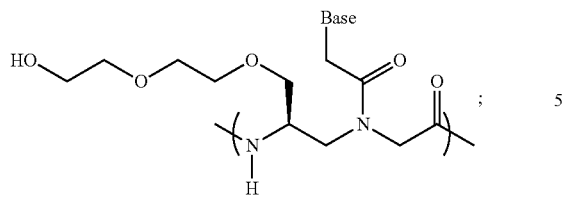

wherein Base is a nucleobase;
wherein the nucleobase sequence of the miniprobe consists of:
 (A) CCCTAA (nucleobases 18-13 of SEQ ID NO: 2), wherein at least one C is replaced with a G-clamp nucleobase;
 (B) CCCTAACCC (nucleobases 18-10 of SEQ ID NO: 2); or
 (C) CCCTAACCCTAA (nucleobases 7-18 of SEQ ID NO: 2).

20. The γPNA miniprobe according to claim 19, wherein the miniprobe comprises at least one detectable label.

21. The γPNA miniprobe according to claim 19, comprising two or more of said mini-PEG modified γPNA monomers.

22. The γPNA miniprobe according to claim 19, wherein all PNA monomers of the miniprobe are said mini-PEG modified γPNA monomers.

23. The γ-RNA miniprobe according to claim 19, wherein at least one mini-PEG modified γPNA monomer comprises a fluorophore.

\* \* \* \* \*

UNITED STATES PATENT AND TRADEMARK OFFICE
CERTIFICATE OF CORRECTION

PATENT NO. : 9,926,592 B2
APPLICATION NO. : 14/357874
DATED : March 27, 2018
INVENTOR(S) : Bruce A. Armitage et al.

It is certified that error appears in the above-identified patent and that said Letters Patent is hereby corrected as shown below:

In the Specification

In Column 1, Lines 13-16 please delete "This invention was made with United States government support under Grant No. ES0515052 awarded by the National Institutes of Health. The United Sates government has certain rights in this invention." and insert -- This invention was made with government support under Grant Nos. GM080994 and ES015052 awarded by the National Institutes of Health. The government has certain rights in the invention. --

Signed and Sealed this
Twenty-fifth Day of June, 2019

Andrei Iancu
*Director of the United States Patent and Trademark Office*